United States Patent
Lee et al.

(10) Patent No.: US 11,654,126 B2
(45) Date of Patent: May 23, 2023

(54) METHOD OF INHIBITING THE PROLIFERATION OF T AND/OR B LYMPHOCYTES VIA DIMETHYLARGININE DERIVATIVES AND LYMPHOCYTES PROLIFERATION INHIBITOR

(71) Applicant: GUANGZHOU MEDICAL UNIVERSITY, Guangzhou (CN)

(72) Inventors: Jongdae Lee, Guangzhou (CN); Fengyuan Yang, Guangzhou (CN); Liya Shen, Luohe (CN)

(73) Assignee: GUANGZHOU MEDICAL UNIVERSITY, Guangzhou (CN)

( * ) Notice: Subject to any disclaimer, the term of this patent is extended or adjusted under 35 U.S.C. 154(b) by 5 days.

(21) Appl. No.: 16/992,111

(22) Filed: Aug. 13, 2020

(65) Prior Publication Data

US 2021/0196660 A1    Jul. 1, 2021

(30) Foreign Application Priority Data

Dec. 26, 2019   (CN) .......................... 201911366970.2

(51) Int. Cl.
*A61K 31/198*    (2006.01)
*A61P 35/04*    (2006.01)

(52) U.S. Cl.
CPC ............ *A61K 31/198* (2013.01); *A61P 35/04* (2018.01)

(58) Field of Classification Search
CPC .............................. A61K 31/198; A61P 35/04
See application file for complete search history.

(56) References Cited

U.S. PATENT DOCUMENTS

2011/0293525 A1* 12/2011 Radosevich ......... C12N 5/0695
435/26

OTHER PUBLICATIONS

Rodionov et al., Nephrology, Dialysis, Transplantation (2014), 29(11), 2035-2042.*
Xu, "Effect of ADMA on maturation and function of dendritic cells drived from monocyte." Master's thesis, Apr. 2009, Medical college of Zhejiang University, Zhejiang University.
Jens Martens-Lobenhoffer, et al., "Probing AGXT2 enzyme activity in mouse tissue by applying stable isotope-labeled asymmetric dimethyl arginine as substrate." Journal of Mass Spectrometry, vol. 47, Oct. 2012, pp. 1594-1600.
Jens Martens-Lobenhoffer, et al., "Detection and quantification of α-keto-δ-(N(G),N(G)-dimethylguanidino) valeric acid: a metabolite of asymmetric dimethylarginine." Analytical Biochemistry, vol. 419, Aug. 2011, pp. 234-240.
Hiroyuki Yoshitomi, et al., "A role for fungal β-glucans and their receptor Dectin-1 in the induction of autoimmune arthritis in genetically susceptible mice." The Journal of Experimental Medicine, vol. 201, No. 6, Mar. 2005, pp. 949-960.

* cited by examiner

*Primary Examiner* — Shobha Kantamneni
(74) *Attorney, Agent, or Firm* — Muncy, Geissler, Olds & Lowe, P.C.

(57) ABSTRACT

The present invention belongs to the technical field of immunotherapy. A method of using dimethylarginine derivatives to inhibit the proliferation of lymphocyte. ADMA, SDMA, and their derivative DMGV can inhibit T cells and/or B cells proliferation in vitro by inducing mitochondrial ROS. ADMA and SDMA can induce mitochondrial ROS generation by the action of alanine-glyoxylate aminotransferase 2 (AGXT2), which converts both ADMA and SDMA into dimethylguanidino valeric acid (DMGV) in the mitochondria. The dimethylarginine dimethylamino hydrolase (DDAH) inhibitor PD404182 also inhibits T cell proliferation by allowing more ADMA and SDMA to be converted to DMGV. As a clinical relevance, DMGV effectively treated arthritis in mice which was caused by activated T cells.

2 Claims, 9 Drawing Sheets
Specification includes a Sequence Listing.

METHOD OF INHIBITING THE PROLIFERATION OF T AND/OR B LYMPHOCYTES VIA DIMETHYLARGININE DERIVATIVES AND LYMPHOCYTES PROLIFERATION INHIBITOR

CROSS-REFERENCE TO RELATED APPLICATION

This application claims the priority from Chinese Patent Application serial no. 201911366970.2, filed on Dec. 26, 2019. The entirety of the above-mentioned patent application is hereby incorporated by reference herein and made a part of this specification.

FIELD OF THE INVENTION

The present invention relates to the field of immunotherapy, in particular to a method of inhibiting the proliferation of T and/or B lymphocytes via dimethylarginine derivatives and lymphocytes proliferation inhibitor.

BACKGROUND OF THE INVENTION

Immunity is human's physiologic function. The human body relies on the function to differentiate "self" and "non-self" components in order to eliminate non-self antigens that enter the human body, or the damaged cells and tumor cells produced by the human body so that homeostasis, the state of resisting or preventing the infection of microorganisms, parasites or other undesirable organisms, is maintained.

The immune system is composed of immune organs, immune cells and immune active components. Therein, immune cells mainly refer to cells that play an immune role, including phagocytic cells and lymphocytes. Lymphocytes including T cells and B cells are derived from hematopoietic stem cells. The T cell response is cellular immunity whereas the B cell response is humoral immunity. There are two main forms of cellular immunity effects: one is specific binding to and killing target cells by CD8+ T cells; the other is the release of lymphokine by CD4+ T cells, which helps other immune cells to expand and enhance the immunological effect; B cells can differentiate into plasma cells, which can synthesize and secrete antibodies, named immunoglobulin, mainly performing humoral immunity under stimulation.

Autoimmune diseases refer to diseases caused by the body's own tissue damage due to an immune response to self-antigens. Many diseases have been listed as autoimmune diseases, such as systemic lupus erythematosus (SLE), rheumatoid arthritis (RA), inflammatory bowel disease (IBD), psoriasis, allergic asthma, type 1 diabetes (T1D), multiple sclerosis (MS), ankylosing spondylitis, etc. The existing treatment methods for autoimmune diseases are mostly used for specific types of diseases, such as autoimmune liver disease, rheumatoid arthritis and ankylosing spondylitis with specific symptoms, but these methods take life-long course of treatment.

Graft-versus-host disease (GVHD) is a disease caused by an allogeneic transplant. In GVHD, the donor's bone marrow or peripheral blood stem cells view the recipient's body as foreign and attack. Transplant rejection, also called HVGD, occurs when a transplanted tissue or organ is rejected by the recipient's immune system, in which mostly T cells of the host destroy the transplanted tissue. Transplant rejection can be lessened by determining the molecular similitude between donor and recipient and by use of immunosuppressant drugs after transplant. In both diseases, T cells play the essential role.

The causes and mechanisms of autoimmune diseases are complicated. They involve both innate immunity and native immunity. The most basic factor leading to pathogenesis is destruction of the autoimmune tolerance mechanism. Physiologically, high-affinity self-reactive T cells and B cells are removed in central immune organs, and when the autoimmune tolerance mechanism is destroyed, the proliferation of T and B cells activated by self-antigens in the body gets out of control. After reiterative destruction, recognition and amplification processes, tissue-organ specific damage eventually occurs, resulting in a series of autoimmune diseases or chronic inflammatory diseases. The pathogenesis of the above-mentioned autoimmune diseases suggests that inhibiting the abnormal activation and proliferation of T cells and B cells in the body may be a potential treatment of autoimmune diseases as well as organ transplantation.

SUMMARY OF THE INVENTION

In view of the above-mentioned technical problems in the prior art, the present invention has discovered that dimethylarginine derivatives are effective inhibitors of in vitro T cells and/or B cells proliferation, suggesting that they can effectively treat the diseases mediated by T cells and/or B cells. Indeed, in a preclinical trial, DMGV effectively treated arthritis caused by activated T cells.

The object of the present invention is achieved by the following technical aspects:

In one aspect, the present invention provides a method of using dimethylarginine derivatives and/or substances that specifically inhibit the conversion of dimethylarginine to L-citrulline, to inhibit the proliferation of lymphocytes.

Furthermore, the present invention provides a method of using the dimethylarginine derivatives to inhibit the proliferation of lymphocytes; the dimethylarginine derivative is selected from the group consisting of ADMA, SDMA and DMGV; the lymphocyte is selected from T cells and/or B cells.

The present invention found that dimethylarginine (including symmetric dimethylarginine (SDMA) and asymmetric dimethylarginine (ADMA)) can effectively inhibit the proliferation of T cells and/or B cells in vitro, and the mechanism of inhibiting the proliferation of T cells and/or B cells in vivo by ADMA or SDMA was studied. And it was found that dimethylarginine (ADMA or SDMA) can induce the generation of mitochondrial reactive oxygen species (ROS) by the action of mitochondrial glyoxylate aminotransferase (AGXT2). Thus specifically inhibiting the generation of mitochondrial reactive oxygen species can remove the proliferation inhibition caused by ADMA or SDMA. In the absence of AGXT2, either ADMA or SMDA cannot induce ROS generation.

It was determined that ADMA or SDMA induce mitochondrial ROS generation by the action of AGXT2, which converts them to the new substance named dimethylguanidino valeric acid (DMGV). Therefore, ADMA, SDMA, DMGV can effectively inhibit the proliferation of T cells and/or B cells, providing new directions for the treatment of T and/or B cell-mediated diseases; ADMA and SDMA are both by-products of arginine metabolism. They are both small molecules with a molecular weight of 202 and can be secreted by different cell types. And DMGV is a metabolite of ADMA or SDMA.

In other words, when the dimethylarginine derivative is selected from ADMA or SDMA; ADMA or SDMA induce the generation of ROS via AGXT2, specifically inhibiting T cells and/or B cells proliferation.

In some embodiments, a concentration of the ADMA or SDMA is 1 μM to 5 μM when it works in inhibiting T cells and/or B cells proliferation.

In some embodiments, when dimethylarginine derivative is DMGV, it induces the generation of ROS, specifically inhibiting T cells and/or B cells proliferation.

It is known that ADMA or SDMA can be converted to L-citrulline in the cytosol by dimethylarginine dimethylamino hydrolase (DDAH), thus reducing the amount of effective ADMA or SDMA to be converted to DMGV in the mitochondria. The present invention found that the specific DDAH inhibitor PD404182 can thus inhibit T cells proliferation by making more AMDA or SDMA available to AGXT2, and when T cells are in the activated state, the inhibitory effect of ADMA, SDMA, or PD404182 is superior to rapamycin. Therefore, it is reasonable to predict that specific inhibitors of DDAH, such as PD404182, or its derivatives can also inhibit the proliferation of T cells and/or B cells.

Furthermore, the present invention provides a method of using the substances that specifically inhibits the conversion of dimethylarginine to L-citrulline, to inhibit the proliferation of lymphocytes. It can be interpreted as that the substances that specifically inhibit the conversion of dimethylarginine to L-citrulline inhibit the conversion of ADMA or SDMA to L-citrulline by dimethylarginine dimethylamino hydrolase.

In some embodiments, the substances are selected from the group consisting of specific inhibitors of dimethylarginine dimethylamino hydrolase (also named as DDAH) and its derivatives (also named as derivatives of specific inhibitors of DDAH).

In some embodiments, the specific inhibitor of DDAH is PD404182.

In another aspect, the invention also provides an in vitro lymphocyte proliferation inhibitor, comprising dimethylarginine derivatives and/or substances that specifically inhibit the conversion of dimethylarginine derivatives (ADMA/SDMA) to L-citrulline; wherein the lymphocyte is selected from T cells and/or B cells; the dimethylarginine derivative is selected from the group consisting of ADMA, SDMA and DMGV; the substance that specifically inhibits the conversion of dimethylarginine to L-citrulline is PD404182.

In some embodiments, when the dimethylarginine derivative is selected from ADMA or SDMA; ADMA or SDMA induces the generation of ROS by the action of AGXT2, specifically inhibiting T cells and/or B cells proliferation.

In some embodiments, a concentration of the ADMA or SDMA is 1 μM to 5 μM when it works in inhibiting T cells and/or B cells proliferation.

And when the dimethylarginine derivative is DMGV, it induces the generation of ROS, specifically inhibiting T cells and/or B cells proliferation.

In still another aspect, the present invention also provides a method of using dimethylarginine derivatives and/or substances that specifically inhibit the conversion of dimethylarginine to L-citrulline to treat diseases caused by abnormal proliferation of T cells and/or B cells.

On one hand, the present invention provides a method of using dimethylarginine derivatives to treat diseases caused by abnormal proliferation of T cells and/or B cells; wherein the dimethylarginine derivative is selected from the group consisting of ADMA, SDMA and DMGV.

In other words, when the dimethylarginine derivative is selected from ADMA or SDMA; ADMA or SDMA induce the generation of ROS by the action of AGXT2, specifically inhibiting T cells and/or B cells proliferation.

And when the dimethylarginine derivative is DMGV, it induces the generation of ROS, specifically inhibiting T cells and/or B cells proliferation.

In some embodiments, the diseases caused by abnormal proliferation of T cells and/or B cells include autoimmune diseases and chronic inflammatory diseases.

In some embodiments, the autoimmune diseases and chronic inflammatory diseases include, graft-versus-host disease, rheumatoid arthritis, inflammatory bowel disease, systemic lupus erythematosus, psoriasis, allergic asthma, type 1 diabetes, multiple sclerosis, ankylosing spondylitis and T cell lymphoma.

On the other hand, the present invention provides a method of using substances that specifically inhibit the conversion of dimethylarginine to L-citrulline to treat diseases caused by abnormal proliferation of T cells and/or B cells.

In some embodiments, the substances are selected from the group consisting of specific inhibitors of dimethylarginine dimethylamino hydrolase (also named as DDAH) and its derivatives (also named as derivatives of specific inhibitors of DDAH).

In some embodiments, the specific inhibitor of DDAH is PD404182.

In some embodiments, the diseases caused by abnormal proliferation of T cells and/or B cells include autoimmune diseases and chronic inflammatory diseases.

In some embodiments, the autoimmune diseases and chronic inflammatory diseases include, graft-versus-host disease, rheumatoid arthritis, inflammatory bowel disease, systemic lupus erythematosus, psoriasis, allergic asthma, type 1 diabetes, multiple sclerosis, ankylosing spondylitis and T cell lymphoma.

BRIEF DESCRIPTION OF THE DRAWINGS

FIG. 3A and FIG. 3B show the effect of ADMA or SDMA on the proliferation of mouse B cells.

FIG. 6A, FIG. 6B, FIG. 6C, and FIG. 6D show DMGV inhibits T cells proliferation via induction of mitochondrial ROS.

DETAILED DESCRIPTION OF THE ILLUSTRATED EMBODIMENTS

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination.

Lymphocyte: The term "lymphocyte" as used herein refers to T cells and B cells.

Proliferation: The term "proliferation" as used herein refers to division of cells.

Inhibit or inhibiting: The term "inhibit" or "inhibiting" as used herein refers to prohibit or prohibiting from doing something such as proliferation.

Treatment or treating: The term "treatment" or "treating" as used herein refers to therapeutic treatment wherein the object is to slow down (lessen) if not cure the targeted pathologic condition or disorder or prevent recurrence of the condition.

Inhibitor: The term "inhibitor" as used herein refers to a compound or molecule that blocks a specific function.

Degradation of dimethylarginine: The term "degradation of dimethylarginine" as used herein refers to metabolic decomposition of dimethylarginine.

Abnormal proliferation: The term "abnormal proliferation" as used herein refers to either less or more proliferation than the control cells.

Induce, induction or inducing: The term "induce", "induction" or "inducing" as used herein refers to cause, or causing.

Throughout, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 5 should be considered to have specifically disclosed sub-ranges such as from 1 to 3, from 1 to 4, from 2 to 4, from 3 to 5 etc., as well as individual numbers within that range, for example, 1, 2, 3, 4, and 5. This applies regardless of the breadth of the range.

Other objects, advantages and features of the present invention will become apparent from the following specification taken in conjunction with the accompanying drawings.

In order to show a clear understanding of the technical features, purposes and effects of the present invention, the specific embodiments of the present invention will now be described in detail with reference to the drawings. Obviously, the described embodiments are only a part of the embodiments of the present invention, but not all the embodiments. Based on the embodiments of the present invention, all other embodiments obtained by those of ordinary skill in the art without creative work will fall within the protection of the present invention.

ADMA and SDMA are purchased from Sigma; RPMI and other cell culture media from Gibco; fetal bovine serum from BI (Biological Industries); CellTrace, CellROX Green, anti-IgM, recombinant human IL-4 from Thermo Fisher Scientific; MitoQ from Caymen Chemical; The anti-mouse CD19 antibody (FITC) from Bio Legend.

Primary cell growth conditions: T cells and/or B cells are cultured with RPMI-1640 (containing 10% FBS) in an incubator with 5% carbon dioxide.

Mice: All experimental animals are kept in the SPF animal house of Guangzhou University of Chinese Medicine, C57BL mice are purchased from Jinan Pengyue Experimental Animal Center. The mice used in the following experiment are female of 6-8 weeks old.

Embodiment 1 ADMA and SDMA Inhibit Mouse T Cell Proliferation

Step 1. Mouse T Cells Isolation

Total splenic T cells were isolated by StemCell isolation kit: From female 6-8 weeks old C57BL mice, spleens were harvested, mechanically disrupted, and incubated with a biotinylated antibody cocktail consisting of antibodies to B220, CD11b, CD11c, CD16/32, CD19, CD25, CD105, NK1.1, and TCRγδ (StemCell). After a wash step, cells were incubated with streptavidin-coated magnetic nanoparticles (StemCell). $CD3^+$ cells were then isolated by applying a magnetic field and collecting the unbound cells.

Step 2. Inhibition of ADMA and SDMA on Mouse T Cells Proliferation

The total T cells obtained in step 1 were labeled with the proliferation indicator dye CellTrace Violet according to the manufacturer's protocol, and then seeded in 96-well round bottom cell culture plates at 2×10$^5$ per well, next the cells were stimulated with anti-CD3 and anti-CD28 antibody coated magnetic beads (Gibco Dynabeads mouse T-activator CD3/CD28 for T-cell expansion and activation) with the beads to cells ratio of 1:4, and then expanded in RPMI-1640 medium up to 4 days, and dilution of CellTrace Violet was then evaluated by flow cytometry.

Experimental group: different concentrations of ADMA or SDMA were added (ADMA and SDMA dissolved in sterile endotoxin-free water, and the concentration of the storage solution is 0.5 mM); Control group: the same volume of sterile endotoxin-free water was added without ADMA or SDMA.

Figure 1A:
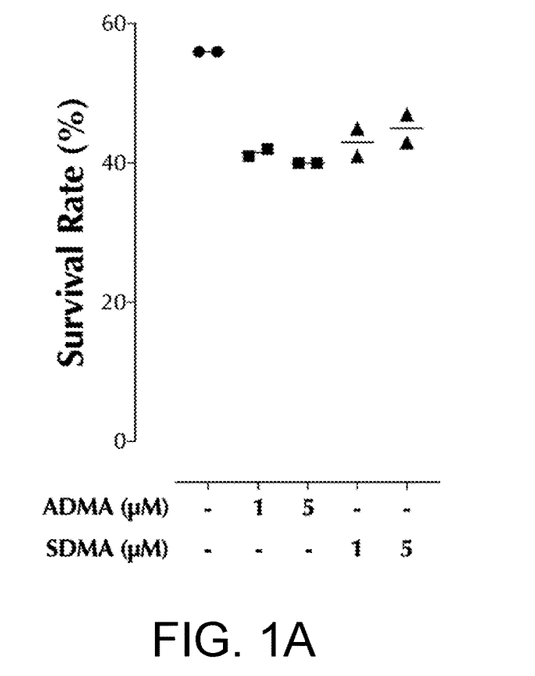
FIG. 1A and FIG. 1B show the effect of ADMA or SDMA on the proliferation of mouse T cells; after 3 days of stimulation, the survival rate (FIG. 1A) and the divided cells count (FIG. 1B) were measured by flow cytometry.
Figure 1B:
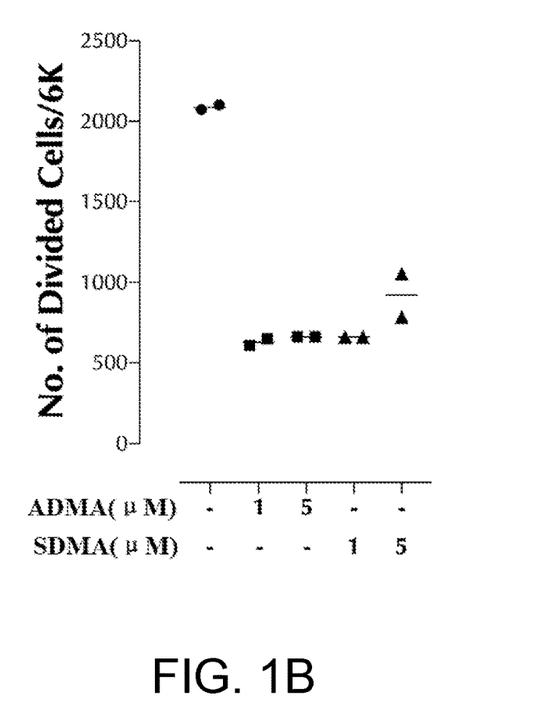

The experimental results are shown in FIG. 1A and FIG. 1B. As we can see: compared with the control group, in the experimental group, both ADMA and SDMA at a concentration of 1 µM and 5 µM, respectively, reduced the survival rate of cells; as we can see in FIG. 1B: both ADMA and SDMA at a concentration of 1 µM and 5 µM, respectively, resulted in the reduction of the number of divided T cells. From the research, it can be concluded that ADMA or SDMA can significantly inhibit the proliferation of mouse T cells at 1 µM and 5 µM (P<0.001), This is the first of such demonstration of their effects on T cells.

Embodiment 2 ADMA and SDMA Inhibit Human T Cells Proliferation

Human T cell isolation and in vitro proliferation experiments: the use of blood from healthy adult blood donors was approved by the Ethics Committee of the Medical Faculty of Guangzhou Medical University, Guangzhou, China. Peripheral blood mononuclear cells (PBMCs) were isolated using Sepmate PBMC isolation tubes following the manufacturer's instructions (StemCell). CD3$^+$ human T cells were positively isolated by magnetic cell sorting (Miltenyi Biotec, Bergisch-Gladbach, Germany). Purified T cells were labeled with the proliferation dye CellTrace Violet according to the manufacturer's protocol. Then the cells (1×10$^5$ cells per well in flat bottom 96 well plate) were stimulated in vitro with immobilized anti-CD3 (5 µg/ml) and anti-CD28 (2 µg/ml) antibody (Biolegend, San Diego, USA), and expanded in RPMI1640 medium up to 5 days. Dilution of CellTrace Violet, indicating proliferation, was then evaluated by flow cytometry.

Figure 2:
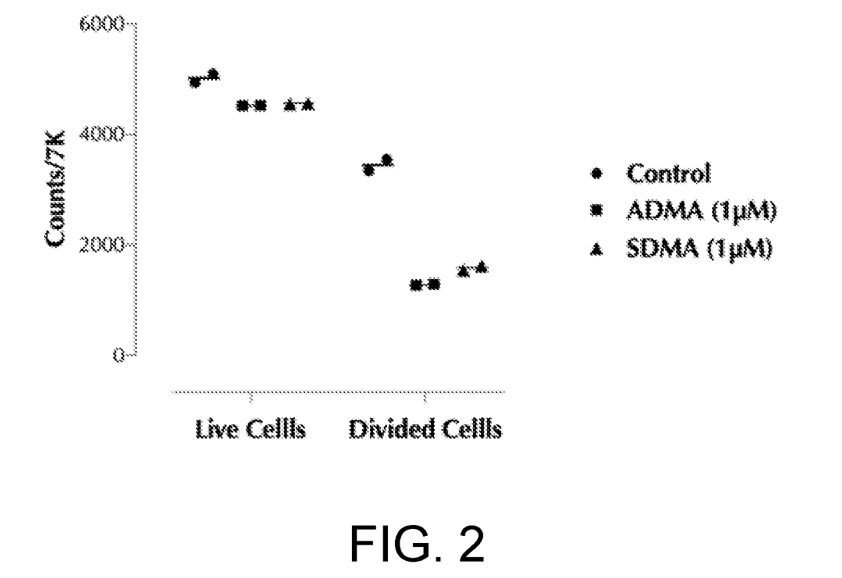
FIG. 2 shows the effect of different concentrations of ADMA or SDMA on the number of live and divided T cells; T cell proliferation assay was set up with or without addition of 1 μM of ADMA or SDMA. After 4 days, the numbers of live and divided cells were counted by flow cytometry.

The experimental results are shown in FIG. 2. As we can see: after 4 days of culture, both ADMA and SDMA at a concentration of 1 µM reduced the number of divided T cells. From the research, it can be concluded that both ADMA and SDMA can inhibit proliferation of human T cells significantly (P<0.001) at 1 µM.

Embodiment 3 ADMA and SDMA Inhibit Mouse B Cells Proliferation

Step 1. Isolation of Total Splenocytes

Spleens were harvested, mechanically disrupted, and resuspend in RPMI 1640 complete medium (10% FBS).

Step 2. B Cells Proliferation Assay

Total splenocytes were then labeled with the proliferation dye CellTrace Violet according to the manufacturer's protocol. Then splenocytes (1×10$^5$ cells per well in flat bottom 96 well plate) were stimulated with recombinant human IL-4 (1 Ong/me and α-mouse IgM (10 µg/ml), and expanded in RPMI1640 medium up to 5 days. Dilution of CellTrace Violet was then evaluated by flow cytometry. (Note; splenocytes contain T cells and monocytes, which will die off during the assay period.)

Experimental group: ADMA or SDMA (5 µM) was added (ADMA and SDMA dissolved in sterile endotoxin-free water, the storage solution concentration is 0.5 mM). Control group: the same volume of sterile endotoxin-free water without ADMA or SDMA was added.

Figure 3A:
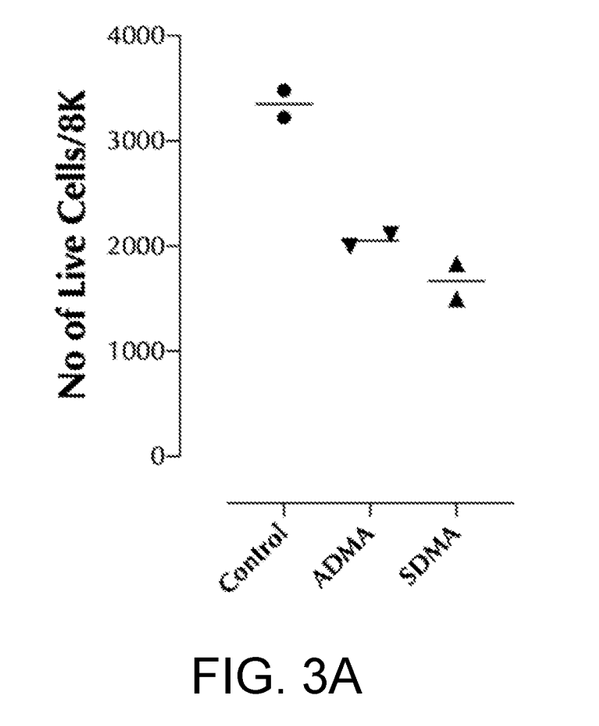
FIG. 3A shows the effect of ADMA or SDMA on the number of live cells.
Figure 3B:
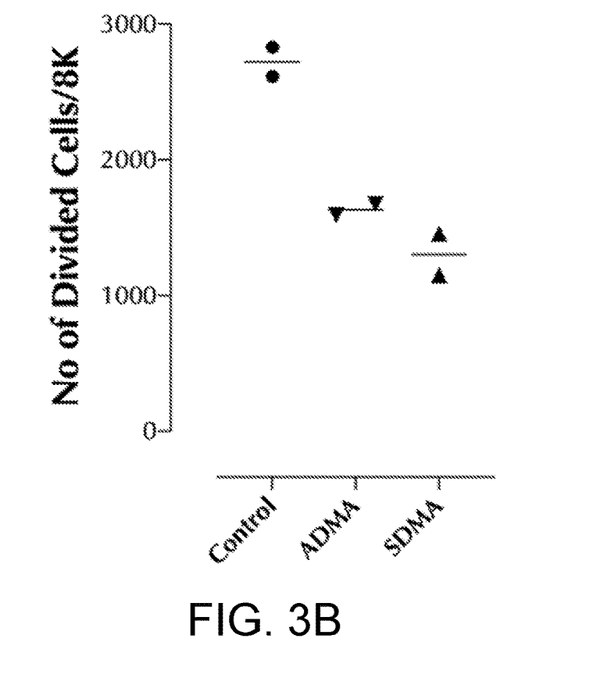
FIG. 3B shows the effect of ADMA or SDMA on the number of divided cells; B cell proliferation assay was set up with or without addition of 5 μM of ADMA or SDMA. After 4 days, the numbers of live cells and divided cells were counted by flow cytometry.

The experimental results are shown in FIG. 3A and FIG. 3B. As can be seen, both ADMA and SDMA reduced the number of live (FIG. 3A) and divided B cells (FIG. 3B). From the research it can be concluded that ADMA or SDMA can significantly inhibit B cells proliferation (P<0.01).

Embodiment 4 Mechanism of Inhibiting T Cells Proliferation

1. The Effect of ADMA and SDMA on Mitochondrial ROS Generation

For flow cytometry, T cells were stained with 5 µM CellROX Green Reagent (Life Technologies) for 30 min at 37° C. in the presence or absence of ADMA or SDMA (5 µM), and then washed with 1×PBS once. MitoQ (100 nM) was added with ADMA and SDMA. Cells were resuspended in 300 µl of PBS before the analysis by flow cytometry.

Experimental Groups: ADMA alone, SDMA alone, or ADMA/SDMA (ADMA/SDMA represents the mixture of ADMA and SDMA herein) was used at the final concentration of 1 µM, MitoQ was used either at 10 nM or 100 nM.

The results are shown in FIG. 4A, FIG. 4B, FIG. 4C, and FIG. 4D. As can be seen from FIG. 4A: compared with the experimental group with none, ROS was significantly induced by ADMA or SDMA. As can be seen from FIG. 4B: compared with the experimental group in the absence of MitoQ and ADMA/SDMA, ROS of the experimental group in the presence of ADMA/SDMA alone increased significantly, indicating that ADMA and SDMA induce reactive oxygen species (ROS) in mouse T cells; compared with the experimental group in the presence of ADMA/SDMA alone, ROS of the experimental group in the presence of both MitoQ (100 nM) and ADMA/SDMA decreased significantly, suggesting that ADMA and SDMA induce ROS in the mitochondria of T cells since MitoQ specifically inhibits generation of mitochondrial ROS.

2. Preparation of mouse T cells with AGXT2 gene silencing (also named as AGXT2 knock down, KD) (for specific preparation procedures, refer to Rodionov, R N, Trends Pharmacol Sci)

2.1. RNA Extraction and Reverse Transcription

Total RNA was extracted from cells, using TRIzol method according to the manufacturer's protocol (Thermo Fisher Scientific). Extracted RNA was dissolved in RNase-free and DNase-treated water and then immediately reverse-transcribed using HiScript Q RT SuperMix for qPCR (Vazyme, China). cDNA was stored at −20° C. for subsequent qPCR (quantitative PCR) analyses.

2.2. qPCR qPCR reactions were performed with ChamQ Universal SYBR qPCR Master Mix (Vazyme, Biotech) in LightCycler® 480 Instrument (Roche, Basel, Switzerland).

PCR primers are all from TSINGKE Biologcal Technology (China), siRNA from GenePharma (China), and the related sequences are shown as SEQ ID NO: 1-5.

```
GAPDH primer
GAPDH-F(SEQ ID NO: 1):
5'-TGGATTTGGACGCATTGGTC-3';

GAPDH-R(SEQ ID NO: 2)
5'-TTTGCACTGGTACGTGTTGAT-3';

AGXT2 primer
AGXT2-F(SEQ ID NO: 3):
5'-CAGATAGACCGCCTGTGGCATA-3';

AGXT2-R(SEQ ID NO: 4):
5'-GGCTTCTGATCCACTGTTCACC-3';

AGXT2 siRNA(SEQ ID NO: 5):
5'-UGAAAGAUACCAGUCCCUUTT-3'.
```

2.3. Gene Silencing siRNA was electroporated into mouse T cells using Thermofisher Neon Transfection system at the density of 2.5× $10^6$/ml. Cells were resuspended in transfection buffer provided by the kit. siRNA (150 µM) was mixed with cells at the siRNA to cell volume ratio of 1:10. Then the electroporation was performed according to the protocol (pulse voltage: 2000V, pulse width: 15 ms, pulse number: 2, tip type: 100 µl).

Transfected cells were cultured in IMDM from Gibco supplemented with 10% FBS for 24 h and used for the ROS assay.

2.4. Effect of ADMA/SDMA on the Mouse T Cells (AGXT2 KD) Incubating the AGXT2 KD Mouse T Cells and ADMA/SDMA.

Figure 4A:
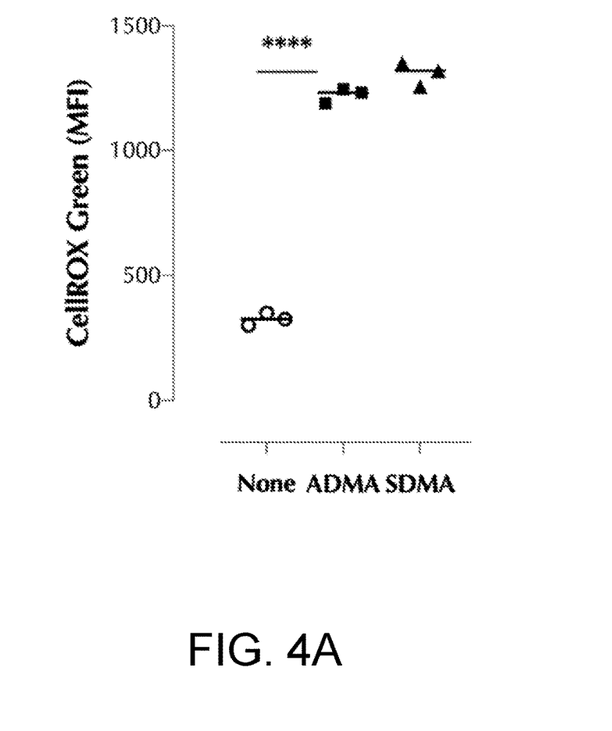
FIG. 4A, FIG. 4B, FIG. 4C, and FIG. 4D show a mechanism study of ADMA and/or SDMA inhibiting T cell proliferation; ROS was measured by flow cytometry 2 hours after adding ADMA or SDMA (5 μM)(FIG. 4A); ROS was measured by flow cytometry 2 hours after adding ADMA and/or SDMA in the presence and/or absence of MitoQ (FIG. 4B); ROS was measured 2 hours after adding ADMA plus SDMA in the control and the AGXT2 knockdown (KD) T cells (FIG. 4C); T cell proliferation was measured after 3 days in cells treated with nothing, ADMA/SDMA (1 μM), or ADMA/SDMA (1 µM) plus MitoQ (100 nM). After 3 days, the divided cell counts were measured by flow cytometry (FIG. 4D).
Figure 4B:
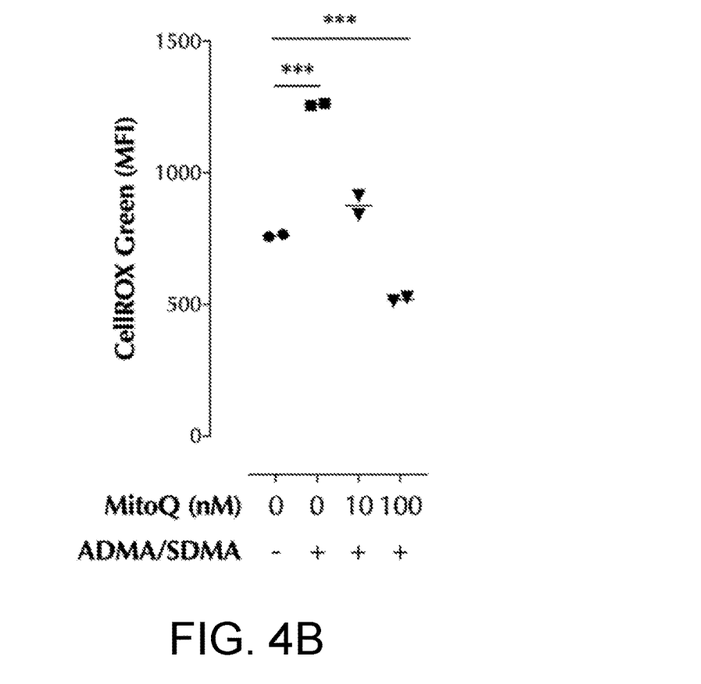
Figure 4C:
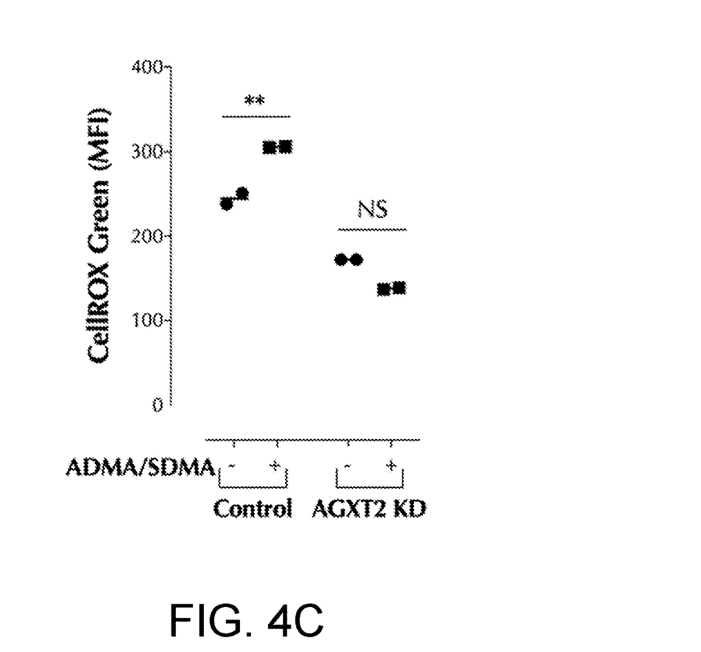

FIG. 4C is the ROS induction results after incubating the AGXT2 KD mouse T cells with 1 µM ADMA/SDMA for 2 hours. It can be seen from FIG. 4C: In the control cells, the addition of ADMA/SDMA induced the generation of ROS in T cells. However, when the AGXT2 gene of T cells is silenced, there is no significant generation of ROS in the T cells with ADMA/SDMA, indicating that ADMA and SDMA should be converted into DMGV (dimethylguanidino valeric acid) via AGXT2 in the mitochondria to generate ROS.

3. The Effect of MitoQ on T Cell Proliferation In Vitro

After incubating MitoQ and ADMA/SDMA together with T cells up to 3 days, flow cytometry was used to investigate the effect on the T cells proliferation in vitro.

Experimental groups: Control, ADMA/SDMA (1 µM), and ADMA/SDMA (1 µM)+MitoQ (100 nM).

Figure 4D:
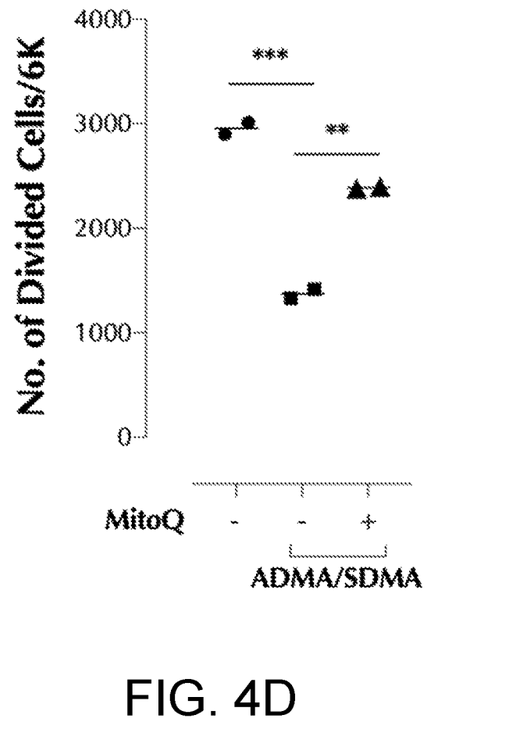

The results were shown in FIG. 4D. Compared with the control group (the group without MitoQ and ADMA/SDMA), the ADMA/SDMA group significantly inhibited T cells proliferation. Compared with the ADMA/SDMA group, the ability of ADMA/SDMA+MitoQ (100 nM) group to inhibit cell proliferation was significantly decreased. From the research it can be concluded that MitoQ can significantly prevent the inhibitory effect of ADMA and SDMA on T cells proliferation.

In summary, it can be concluded that ADMA or SDMA is converted to DMGV in mitochondria by AGXT2, which induces ROS, and the ROS generated by DMGV inhibits T cells proliferation.

Embodiment 5 Dimethylarginine Dimethylamino Hydrolase (DDAH) Inhibitor PD404182 Inhibits Activated T Cells Proliferation Human T cells were stimulated with anti-human CD3 and CD28 for 24 hours. ADMA (1 µM), DDAH inhibitor PD404182 (100 nM) or rapamycin (50 nM) was respectively added and incubated for additional 3 days. Flow cytometry was used to analyze the number of live cells and the number of divided cells. The results are shown in FIG. 5A and FIG. 5B, respectively.

Figure 5A:
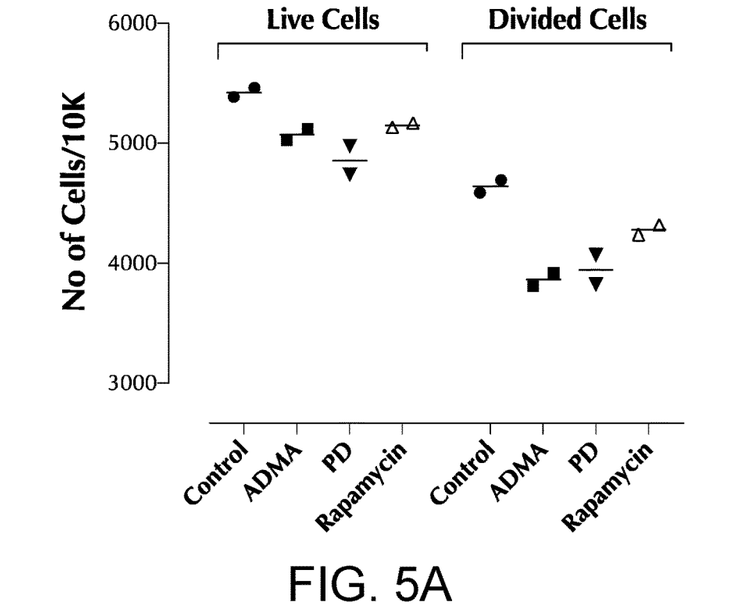
FIG. 5A and FIG. 5B show the effect of DDAH inhibitor PD404182 (also named PD herein) on activated human T cells; Human T cells were stimulated for 24 hours and then ADMA (1 µM), PD404182 (100 nM), or rapamycin (50 nM) was added. The numbers of live and divided cells were measured after 24 hours (FIG. 5A) and 48 hours (FIG. 5B) later.
Figure 5B:
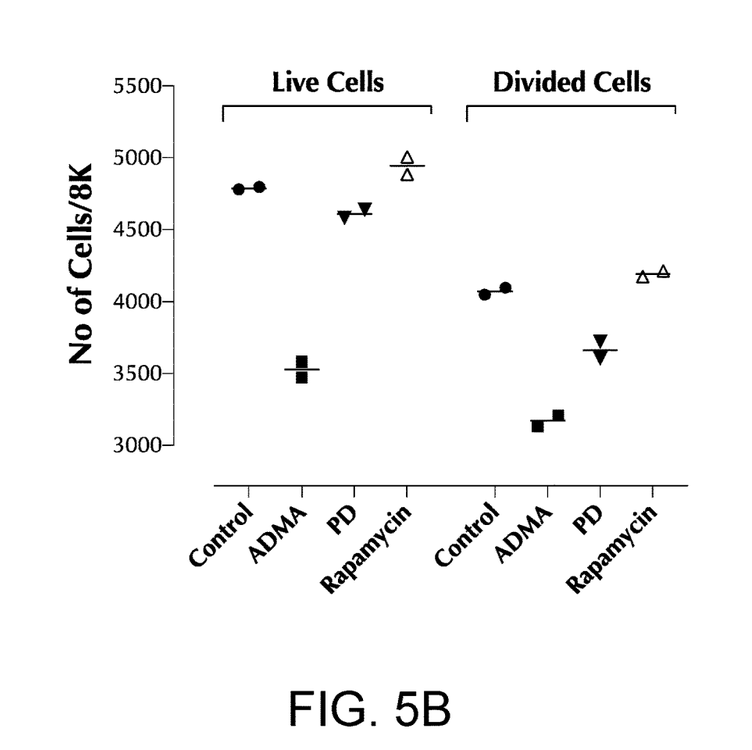

It can be seen from FIG. 5A and FIG. 5B that the number of live cells in the control and rapamycin group are basically the same, but after adding ADMA or PD404182, the number of live cells declined after 24 h (FIG. 5A) and 48 h (FIG. 5B). In addition, compared with the control or the rapamycin group, after adding ADMA, the number of divided cells of T cells decreased significantly, and the decline is more pronounced than PD404182; it can be seen that both PD404182 and ADMA can inhibit T cell proliferation, and the inhibitory effect of ADMA is better than PD404182, and both of them are superior to the mTOR inhibitor rapamycin.

In summary, it can be seen that ADMA or SDMA can be converted to L-citrulline by dimethylarginine dimethylamino hydrolase (DDAH), thus reducing the amount of effective ADMA or SDMA which enters the mitochondria and is converted to DMGV. The specific DDAH inhibitor PD404182 can also inhibit T cells proliferation, and when T cells are in the activated state, their inhibitory effect is superior to rapamycin.

Therefore, it is reasonable to predict that specific inhibitors of DDAH, such as PD404182, or its derivatives, can also inhibit the proliferation of T cells and/or B cells.

Embodiment 6 DMGV Inhibits T Cell Proliferation Via Induction of Mitochondrial ROS DMGV was synthesized as described in the literature (for specific preparation procedures, refer to J. Mass Spectrom. 2012, 47, 1594; Anal. Biochem. 2011, 419, 234). Mouse and human T cells were treated with none, or DMGV (10 µM), or DMGV+MitoQ (100 nM) for 1 h and ROS was measured by flow cytometry. The results are shown in FIG. 6A and FIG. 6B, respectively.

Figure 6A:
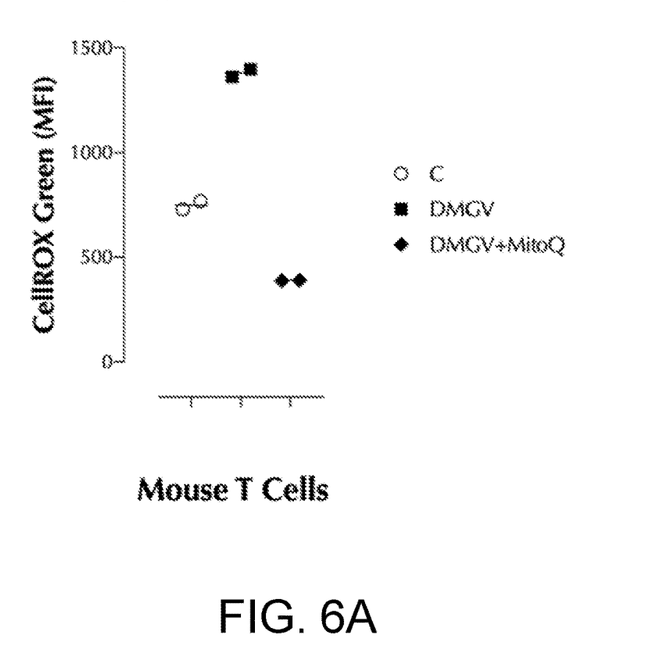
FIG. 6A: Mouse splenic T cells were incubated with none, DMGV (10 µM), or DMGV (10 µM) plus MitoQ (100 nM) for 1 h and ROS was measured by flow cytometry.
Figure 6B:
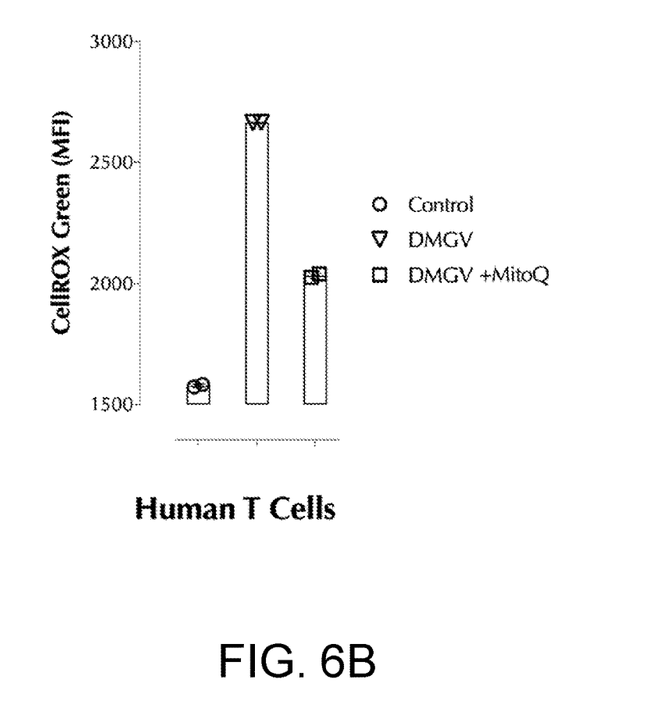
FIG. 6B: Human peripheral T cells were incubated with none, DMGV (10 µM), or DMGV (10 µM) plus MitoQ (100 nM) for 1 h and ROS was measured by flow cytometry.

It can be seen from FIG. 6A and FIG. 6B that DMGV induces ROS in mouse and human T cells, respectively, in the mitochondria, which was inhibited by MitoQ.

Mouse or human T cells were activated by anti-CD3 and anti-28 antibodies with none, DMGV (10 µM), or DMGV+MitoQ (100 nM) for 3 days and proliferation was measured by flow cytometry. The results are shown in FIG. 6C and FIG. 6D, respectively.

Figure 6C:
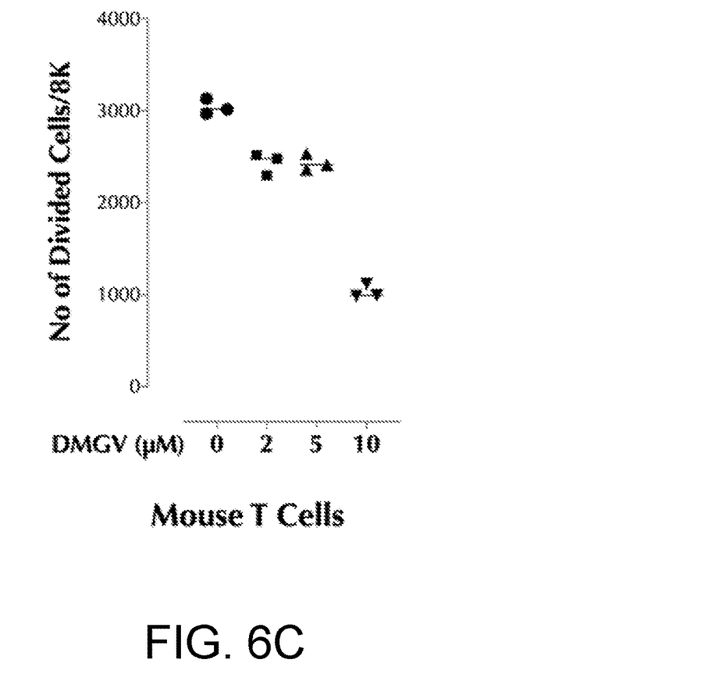
FIG. 6C: Mouse T cells were activated without or with different amounts of DMGV as indicated and proliferation was measured after 3 days by flow cytometry.
Figure 6D:
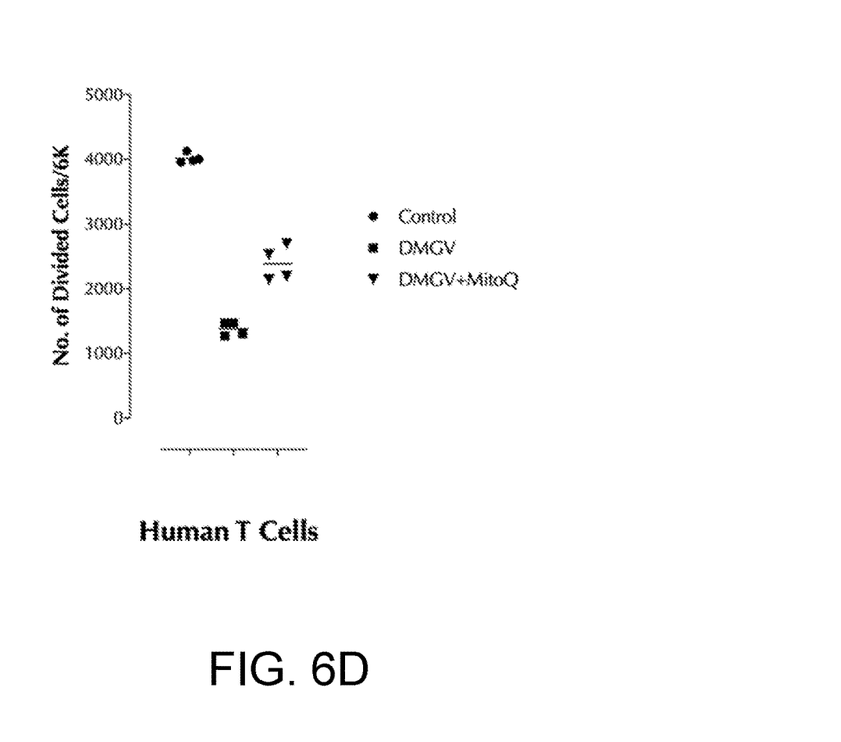
FIG. 6D: Human T cells were activated with none, DMGV (10 µM), or DMGV (10 µM) plus MitoQ (100 nM), and proliferation was measured after 3 days by flow cytometry.

It can be seen from FIG. 6C and FIG. 6D that DMGV inhibited proliferation of both mouse and human T cells by inducing ROS in the mitochondria, which is inhibited by MitoQ.

In summary, it can be seen that DMGV inhibits proliferation of T cells by inducing mitochondrial ROS.

Embodiment 7 DMGV Significantly Reduces Arthritis in Mice

SKG mice (purchased from CLEA Japan, Inc.) develop arthritis because a mutation in the ZAP-70 gene, which causes activation of T cells. SKG mice were injected with beta-glucan (30 mg/mouse, Sigma) to accelerate development of arthritis and the arthritis score was calculated as described in the literature (for specific preparation procedures, refer to Yoshitomi, H, J. Exp Med. 2005). Mice that reached the arthritis score of 8 or above in less than 2 months were selected and treated with DMGV (750 µg/mouse) twice a week up to 50 days.

Figure 7:
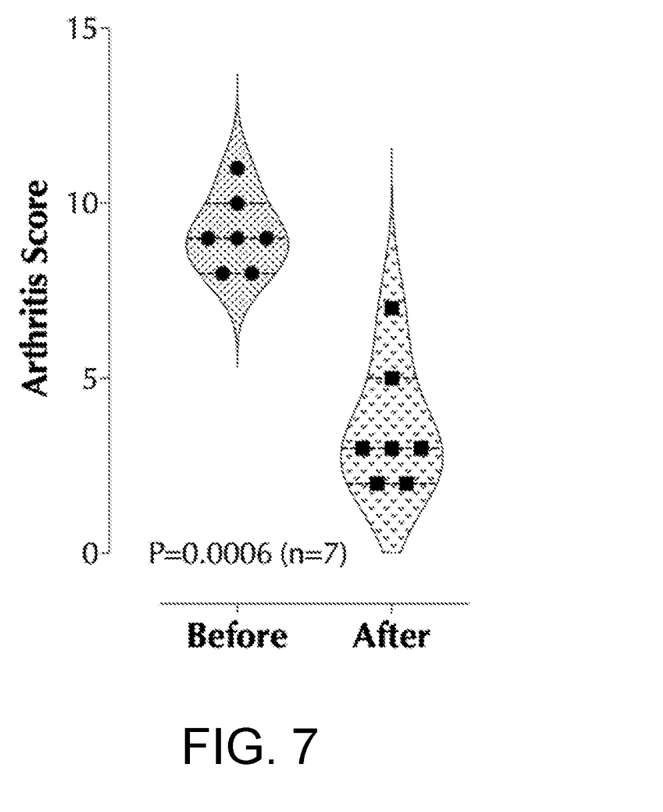
FIG. 7 shows DMGV effectively treated arthritis in mice. SKG mice were injected with beta-glucan (30 mg/mouse), and after 30 to 50 days the mice that reached the arthritis score of 8 or higher (n=7) were selected for treatment. The selected mice were treated every 3 days with DMGV (750 µg/mouse/injection in the peritoneum) up to 50 days. The statistical significance was calculated by 2-way ANOVA and a P value less than 0.05 is considered as significant.

It can be seen from FIG. 7 that DMGV significantly decreased the arthritis score in all mice (N=7, P=0.0006 calculated by 2-way ANOVA). Each dot represents an individual mouse.

What is claimed is:

1. A method to treat rheumatoid arthritis, comprising administering to a subject in need thereof an effective amount of 750 µg dimethylguanidino valeric acid (DMGV) twice a week for 50 days.

2. The method according to claim 1, wherein DMGV induces the generation of ROS, specifically inhibiting T cells and/or B cells proliferation.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Mouse

<400> SEQUENCE: 1
tggatttgga cgcattggtc                          20

<210> SEQ ID NO 2
<211> LENGTH: 21
<212> TYPE: DNA
<213> ORGANISM: Mouse

<400> SEQUENCE: 2
tttgcactgg tacgtgttga t                        21

<210> SEQ ID NO 3
<211> LENGTH: 22
<212> TYPE: DNA
<213> ORGANISM: Mouse

<400> SEQUENCE: 3
cagatagacc gcctgtggca ta                       22

<210> SEQ ID NO 4
<211> LENGTH: 22
<212> TYPE: DNA
<213> ORGANISM: Mouse

<400> SEQUENCE: 4
ggcttctgat ccactgttca cc                       22

<210> SEQ ID NO 5
<211> LENGTH: 19
<212> TYPE: RNA
<213> ORGANISM: Mouse

<400> SEQUENCE: 5
ugaaagauac cagucccuu                           19